US010179005B2

(12) United States Patent
Endo (10) Patent No.: US 10,179,005 B2
(45) Date of Patent: Jan. 15, 2019

(54) MEDICAL KNIFE

(71) Applicant: KAI R & D CENTER CO., LTD., Seki-shi, Gifu (JP)

(72) Inventor: Masahiro Endo, Seki (JP)

(73) Assignee: Kai R & D Center Co., Ltd., Gifu (JP)

( * ) Notice: Subject to any disclaimer, the term of this patent is extended or adjusted under 35 U.S.C. 154(b) by 10 days.

(21) Appl. No.: 15/349,672

(22) Filed: Nov. 11, 2016

(65) Prior Publication Data
US 2017/0135716 A1 May 18, 2017

(30) Foreign Application Priority Data
Nov. 12, 2015 (JP) ................ 2015-222039

(51) Int. Cl.
| A61B 17/3211 | (2006.01) |
| A61B 17/3213 | (2006.01) |
| B26B 5/00 | (2006.01) |
| A61B 17/00 | (2006.01) |

(52) U.S. Cl.
CPC ...... *A61B 17/3211* (2013.01); *A61B 17/3213* (2013.01); *B26B 5/008* (2013.01); *A61B 2017/00473* (2013.01); *A61B 2017/00831* (2013.01)

(58) Field of Classification Search
CPC ... A61B 17/3211; A61B 17/3213; B26B 3/04; B26B 5/00; B26B 5/008
USPC ................ 30/152, 304; 606/167; D24/147
See application file for complete search history.

(56) References Cited

U.S. PATENT DOCUMENTS

| 104,706 A | * | 6/1870 | Codding | .............. B26B 3/04 |
| | | | | 30/304 |
| 172,739 A | * | 1/1876 | Hoffman | ............. B26B 3/04 |
| | | | | 30/304 |
| 206,629 A | * | 7/1878 | Smith | ................ B23D 51/14 |
| | | | | 30/304 |
| 319,294 A | * | 6/1885 | Millspaugh | ........... F16M 11/10 |
| | | | | 30/304 |
| 421,855 A | * | 2/1890 | Burk | ..................... B26B 3/04 |
| | | | | 30/304 |
| 527,002 A | * | 10/1894 | Mayer | ................ B26B 3/04 |
| | | | | 30/304 |
| 595,597 A | * | 12/1897 | Blanchard | ............ B26B 3/04 |
| | | | | 30/304 |

(Continued)

FOREIGN PATENT DOCUMENTS

| DE | 2237374 A1 * | 2/1974 | ............ B26B 5/008 |
| DE | 3629168 A1 * | 2/1988 | ............... B26B 3/04 |

(Continued)

*Primary Examiner* — Jason Daniel Prone
(74) *Attorney, Agent, or Firm* — Norris McLaughlin, P.A.

(57) ABSTRACT

A medical knife that can be assembled with different blade spacings, provided with only one handle includes a pair of side walls on respective sides of the handle, at least in the forward portions of the handle the side walls being formed individually on different handle-constituting parts and a pair of blades separately mounted on the insides of these side walls; and the handle before being assembled to constitute a medical knife is configured such that the two handle-constituting parts forward of a connecting part can be spread apart and closed together, centered on the connecting part, and such that the spacing distance between the two side walls is adjustable.

1 Claim, 9 Drawing Sheets

(56) References Cited

U.S. PATENT DOCUMENTS

| | | | | |
|---|---|---|---|---|
| 608,337 A * | 8/1898 | Merkle | B26B 3/04 | 30/304 |
| 624,737 A * | 5/1899 | Bay | B26B 3/04 | 30/304 |
| 637,463 A * | 11/1899 | Hegarty | B25D 3/00 | 30/304 |
| 639,850 A * | 12/1899 | Hahn | B26B 3/04 | 30/304 |
| D32,329 S * | 3/1900 | Irwin | | 30/304 |
| 655,301 A * | 8/1900 | Hamilton | B26B 3/04 | 30/304 |
| 676,252 A * | 6/1901 | Hester | A47J 17/02 | 30/304 |
| 699,815 A * | 5/1902 | Riddick | B26B 3/04 | 30/304 |
| 719,208 A * | 1/1903 | Garda | B26B 11/00 | 30/304 |
| 719,785 A * | 2/1903 | Garda | B26B 3/04 | 30/304 |
| 726,697 A * | 4/1903 | Kelley | B26B 3/04 | 30/304 |
| 751,251 A * | 2/1904 | Bollinger et al. | B26B 3/04 | 30/304 |
| 760,255 A * | 5/1904 | Roy et al. | B26B 3/04 | 30/304 |
| 797,857 A * | 8/1905 | Kulenkampff | B26B 3/04 | 30/304 |
| 878,293 A * | 2/1908 | Kadan | B43K 17/02 | 30/304 |
| 931,590 A * | 8/1909 | French | A22C 9/008 | 30/304 |
| 939,846 A * | 11/1909 | Matthews | B26B 3/04 | 30/304 |
| 972,225 A * | 10/1910 | Pennell | A47L 13/08 | 30/304 |
| 998,118 A * | 7/1911 | Peterson | B26B 3/04 | 30/304 |
| 1,022,242 A * | 4/1912 | Jackson | A47J 17/02 | 30/304 |
| 1,069,189 A * | 8/1913 | Saltzman | B26B 3/03 | 30/304 |
| 1,081,840 A * | 12/1913 | Koehl et al. | B43K 17/02 | 30/304 |
| 1,116,035 A * | 11/1914 | Doscher | A01F 11/06 | 30/304 |
| 1,128,479 A * | 2/1915 | McPherson | B26B 3/04 | 30/304 |
| D47,697 S * | 8/1915 | Korpa | | 30/304 |
| D47,778 S * | 8/1915 | Yapczenski | | 30/152 |
| 1,176,257 A * | 3/1916 | Velcansky | B26B 3/04 | 30/304 |
| 1,176,317 A * | 3/1916 | Roberts | B26B 3/04 | 30/304 |
| 1,205,871 A * | 11/1916 | Dwyer | B26B 3/04 | 30/304 |
| 1,226,797 A * | 5/1917 | Newman | A47J 17/02 | 30/304 |
| 1,268,558 A * | 6/1918 | Faix et al. | B26B 11/00 | 30/152 |
| 1,278,682 A * | 9/1918 | Kohnz, Jr. | B26B 3/04 | 30/304 |
| 1,280,835 A * | 10/1918 | Preston | B26B 3/04 | 30/304 |
| 1,326,373 A * | 12/1919 | Rice | A47J 17/04 | 30/304 |
| 1,339,698 A * | 5/1920 | Faix et al. | A61B 17/3213 | 30/152 |
| 1,360,765 A * | 11/1920 | Knowlton | A01D 1/00 | 30/304 |
| 1,424,389 A * | 8/1922 | Wyatt | B26D 3/24 | 30/304 |
| 1,441,490 A * | 1/1923 | Duncan | A47J 23/00 | 30/304 |
| 1,444,173 A * | 2/1923 | Duncan | A47J 23/00 | 30/304 |
| 1,530,796 A * | 3/1925 | Thomsen | A21C 5/00 | 30/304 |
| 1,599,800 A * | 9/1926 | Van Sickel | B26B 3/04 | 30/152 |
| 1,614,772 A * | 1/1927 | Bambini et al. | B26B 3/04 | 30/304 |
| 1,649,318 A * | 11/1927 | Miller | A01G 1/06 | 30/304 |
| 1,697,091 A * | 1/1929 | Skubic | B26B 3/04 | 30/304 |
| 1,739,214 A * | 12/1929 | Darling | A22C 9/008 | 30/304 |
| 1,769,525 A * | 7/1930 | Maness | A47G 21/023 | 30/304 |
| 1,810,719 A * | 6/1931 | Lowenthal | A22C 9/008 | 30/304 |
| 1,814,528 A * | 7/1931 | Purcell | B26B 3/04 | 30/304 |
| 1,830,692 A * | 11/1931 | Becker | B26B 5/00 | 30/304 |
| 1,847,062 A * | 2/1932 | Lemmon, Jr. | A21C 15/007 | 30/304 |
| 1,877,211 A * | 9/1932 | Webster | B26B 3/04 | 30/304 |
| D88,766 S * | 12/1932 | Garrett | | 30/304 |
| 1,903,789 A * | 4/1933 | Michaels | B26B 5/008 | 30/304 |
| 1,977,902 A * | 10/1934 | Vermillion | A01G 1/06 | 30/304 |
| 1,991,546 A * | 2/1935 | Czapar, Jr. | A22C 9/008 | 30/304 |
| 2,013,902 A * | 9/1935 | Tarrant | A21C 1/1405 | 30/304 |
| 2,130,949 A * | 9/1938 | Collens | A47J 17/04 | 30/304 |
| 2,210,769 A * | 8/1940 | Muker | A47J 17/00 | 30/304 |
| 2,250,237 A * | 7/1941 | Schwartzkopf | B26B 3/04 | 30/304 |
| 2,364,339 A * | 12/1944 | Becker | C14B 19/00 | 30/304 |
| 2,397,875 A * | 4/1946 | Marshaus | A22C 25/006 | 30/304 |
| 2,448,383 A * | 8/1948 | Mathaus | B26B 3/04 | 30/304 |
| 2,464,206 A * | 3/1949 | Becker | B26B 3/04 | 30/304 |
| 2,507,619 A * | 5/1950 | Anderson | A47K 7/02 | 30/304 |
| 2,528,166 A * | 10/1950 | Orr et al. | B26B 3/04 | 30/304 |
| 2,557,539 A * | 6/1951 | Henrickson | B26B 3/04 | 30/304 |
| 2,637,899 A * | 5/1953 | Conklin | B26B 3/00 | 30/304 |
| 2,745,179 A * | 5/1956 | Jensen et al. | B44C 7/027 | 30/304 |
| 2,962,816 A * | 12/1960 | Glotzer | B26B 3/04 | 30/304 |
| 3,045,348 A * | 7/1962 | Dungan | B26B 5/008 | 30/304 |
| 3,099,307 A * | 7/1963 | Morgan | B26B 3/04 | 30/304 |
| D205,286 S * | 7/1966 | Dyment et al. | | 30/304 |
| 3,270,368 A * | 9/1966 | Cook, Sr. et al. | A22C 25/02 | 30/304 |
| 3,452,754 A * | 7/1969 | Stayer | A61B 17/3213 | 606/167 |
| 3,488,843 A * | 1/1970 | Tims, Jr. | B26B 5/00 | 30/304 |
| 3,998,229 A * | 12/1976 | Barton | A61B 17/3213 | 606/167 |

(56) References Cited

U.S. PATENT DOCUMENTS

| | | | | |
|---|---|---|---|---|
| 4,085,504 A * | 4/1978 | Nagy | B26B 5/008 | 30/304 |
| 4,255,854 A * | 3/1981 | Bilbao | B26B 27/00 | 30/304 |
| 4,288,921 A * | 9/1981 | Rhynes | A21C 11/12 | 30/304 |
| 4,472,879 A * | 9/1984 | Sizemore, Jr. | B26B 3/03 | 30/304 |
| 4,578,865 A * | 4/1986 | Keller | B26B 5/008 | 30/304 |
| 4,969,267 A * | 11/1990 | Anenberg | B26B 3/04 | 30/304 |
| 5,026,385 A | 6/1991 | Schutte et al. | | |
| 5,100,391 A * | 3/1992 | Schutte | A61B 17/3213 | 30/304 |
| D329,699 S * | 9/1992 | Schutte | D24/147 | |
| D330,082 S * | 10/1992 | Schutte et al. | D24/147 | |
| 5,391,169 A * | 2/1995 | McGuire | A61B 17/15 | 30/299 |
| 5,447,516 A | 9/1995 | Gardner | | |
| 5,680,705 A * | 10/1997 | Josoha | B26B 5/008 | 30/304 |
| 5,951,580 A | 9/1999 | Ashraf | | |
| 5,989,273 A * | 11/1999 | Arnold | A61B 17/32093 | 606/167 |
| 6,029,355 A * | 2/2000 | Carlin | B26D 3/001 | 30/304 |
| 6,308,422 B1 * | 10/2001 | MacDonald | B26B 3/04 | 30/304 |
| 6,349,476 B1 * | 2/2002 | Juranitch | A22C 21/0023 | 30/304 |
| 6,381,851 B1 * | 5/2002 | Meyer | A21C 15/04 | 30/304 |
| 6,416,524 B1 * | 7/2002 | Critz | A61B 17/3213 | 606/167 |
| 6,887,250 B1 * | 5/2005 | Dority | A61B 17/3213 | 606/167 |
| 7,255,705 B2 * | 8/2007 | Hsu | B26B 5/008 | 30/304 |
| 7,731,719 B2 * | 6/2010 | Nordt | A61B 17/320016 | 606/79 |
| 7,743,512 B1 * | 6/2010 | Whittemore | B26B 3/04 | 30/299 |
| 8,438,737 B2 * | 5/2013 | Lo | B26B 3/04 | 30/304 |
| 8,572,854 B2 * | 11/2013 | Estoppeij | B26B 3/04 | 30/304 |
| 8,635,781 B2 * | 1/2014 | Fischer | B26B 3/04 | 30/304 |
| D728,325 S * | 5/2015 | Zemel | D7/693 | |
| 2004/0055165 A1 * | 3/2004 | Chan | B26B 5/008 | 30/305 |
| 2009/0100687 A1 * | 4/2009 | Mills | B26B 3/04 | 30/304 |
| 2013/0031790 A1 * | 2/2013 | Lambert | B26B 3/04 | 30/304 |
| 2013/0174425 A1 * | 7/2013 | Neal | A22B 5/0047 | 30/304 |
| 2017/0008178 A1 * | 1/2017 | Cristofaro | B26B 5/008 | 30/304 |

FOREIGN PATENT DOCUMENTS

| | | | | |
|---|---|---|---|---|
| FR | 1195656 A | * | 11/1959 | B26B 5/008 |
| FR | 2682062 A1 | * | 4/1993 | B26B 3/04 |
| FR | 2811929 A1 | * | 1/2002 | B26B 5/008 |
| GB | 1221093 A | * | 2/1971 | B26B 3/04 |
| JP | 58-184647 U | | 12/1983 | |
| JP | 2017086590 A | * | 5/2017 | A61B 17/3213 |

* cited by examiner

MEDICAL KNIFE

BACKGROUND OF THE INVENTION

The present invention relates to a medical knife, in which a pair of blades are mounted in parallel, spaced apart, at the front of a handle.

Medical knives in which a pair of blades are mounted in parallel, spaced apart, as in the present invention, are primarily used to cut tissue at a predetermined width, these being medical knives which are used, for example, in surgery for anterior cruciate ligament reconstruction in the knee, for severing the patellar tendon, for making incisions into bones when collecting tibia plugs or patella plugs, or for collecting tissue at a predetermined widths or the like, while maintaining the spacing of the blades.

Medical knives include those which, after use, are washed and undergo resterilization and are then reused, and those that are disposable. Recently disposable medical knives are often used, in light of the costs of infection prevention and resterilization. The medical knife of the present invention is likewise directed to disposable medical knifes.

Medical knives having two blades are, for example, formed by way of insert molding, in the manner of the knife described in U.S. Pat. No. 5,026,385. In the case of insert molding, the molding is performed with the handle and the blades integrally joined, which facilitates manufacturing and reduces costs, making this a suitable manufacturing method for disposable knives. Normally, in surgeries using medical knives having two blades, knives having differing blade spacings are used as needed. With the knife described in U.S. Pat. No. 5,026,385, it is not possible to adjust the spacing of the two blades, and therefore knives with different blade spacings must be provided. Accordingly, separate molds are necessary in order to manufacture the knives with the different blade spacings, and costs are correspondingly increased. That is to say, if it were possible to manufacture knives having different blade spacings using the same mold, it would be possible to reduce costs.

Knives allowing the spacing between two blades to be adjusted have therefore been proposed, such as the knife described in JP-01-008989-U. However, if this entire knife is used as a disposable item, the manufacturing costs will be high, which has poor profitability.

SUMMARY OF THE INVENTION

An object of the present invention is to provide a medical knife that can be assembled with different blade spacings, even though the handles are molded in the same shape.

The invention according to a first aspect is configured such that a pair of blades protrude, in parallel with each other, with a predetermined spacing therebetween, from the front end of a handle comprising a pair of handle-constituting parts that are connected by a connecting part; a pair of side walls are provided on the two sides of the handle, at least in the forward portions thereof, the side walls being formed individually on different handle-constituting parts, and the pair of blades being separately mounted on the insides of these side walls; and the handle before being assembled in a medical knife is configured such that the two handle-constituting parts forward of the connecting part can be spread apart and closed together, centered on the connecting part, and such that the spacing distance between the two side walls is adjustable.

The aforementioned handle before being assembled in a medical knife of the first aspect is configured such that the handle-constituting parts forward of the connecting part can be spread apart and closed together, centered on the connecting part, and such that the spacing distance between the two side walls is adjustable; the invention described in a second aspect is configured such that at least one of the handle-constituting parts in the pair of handle-constituting parts is formed from a flexible material; the invention described in a third aspect is configured such that the connecting part is formed by a thin hinge; and the invention described in a fourth aspect is configured such that the pair of handle-constituting parts and the connecting part that connects the pair of handle-constituting parts are integrally formed from the same flexible material.

The invention described in a fifth aspect is configured such that a spacing maintenance member for maintaining a constant spacing between the two side walls is mounted between the two side walls.

The invention described in a sixth aspect is configured such that the pair of blades are each separately trapped between the spacing maintenance member and a side wall. The invention described in a seventh aspect is configured such that: an insertion hole is formed in the blades; a fitting hole is formed in the side walls; fitting protrusions are formed on the two sides of the spacing maintenance member; and the fitting protrusions are inserted into the insertion holes in the blades and fitted into the fitting holes in the side walls so as to mount the spacing maintenance member and the blades between the side walls.

The invention described in a eighth aspect is configured such that the handle has a top wall and a bottom wall in a forward portion thereof, on which fingertips can be placed during use, the top wall being formed in a first handle-constituting part and the bottom wall being formed in a second handle-constituting part.

In the first aspect of the invention, a pair of side walls are provided on the two sides of the handle, at least in the forward portions thereof, the side walls being formed individually on different handle-constituting parts, and a pair of blades are separately mounted on the insides of these side walls. Thus, the handle before being assembled in a medical knife is deformable, such that the two handle-constituting parts forward of the connecting part can be spread apart and closed together, centered on the connecting part, and such that the spacing distance between the two side walls is adjustable. Accordingly, when the blades are mounted on the insides of the side walls, the spacing distance between the two side walls is adjustable in keeping with a blade spacing that has been determined in advance, which makes it possible to support knife assemblies with different blade spacings. Furthermore, the handle-constituting parts of the handle before being assembled in a medical knife that is formed is such that the two handle-constituting parts forward of the connecting part can be spread apart and closed together, centered on the connecting part. Accordingly, the handle before assembly can be formed in a configuration in which there is a relative offset between the two side walls, while the spacing between the two side walls is maintained, and the two side walls can be caused to face each other at the time of assembly. Consequently, if the pair of blades are not mounted at the same time on the handle, but rather are mounted on the side walls at different times, the side wall in which the blade is not mounted will not be an obstacle to mounting, such that it will be possible to mount the blade easily.

The invention of the second aspect is configured such that at least one of the handle-constituting parts in the pair of handle-constituting parts is formed from a flexible material;

the invention of the third aspect is configured such that the connecting part is formed by a thin hinge; and the invention of the fourth aspect is configured such that the pair of handle-constituting parts and the connecting part that connects the pair of handle-constituting parts are integrally formed from the same flexible material. Thus, with this configuration, the handle before being assembled in a medical knife is such that the handle-constituting parts forward of the connecting part can be spread apart and closed together, centered on the connecting part, and the spacing distance between the two side walls is adjustable, and thus assembly is easy.

The invention of the fifth aspect is such that a spacing maintenance member for maintaining a constant spacing between the two side walls is mounted between the two side walls. Accordingly, the spacing between the side walls can be easily and accurately ensured by the spacing maintenance member. Furthermore, the spacing between the two side walls can be changed by changing the lateral width of the spacing maintenance member.

The invention of the sixth aspect is configured such that the pair of blades are each separately trapped between the spacing maintenance member and a side wall. Accordingly, if the width, in the spacing direction, of the spacing maintenance member is made to be the same as the intended spacing of the blades, a medical knife having the intended blade spacing the can easily be manufactured. Furthermore, the blade spacing can easily be changed by changing the spacing maintenance member. The invention of the seventh aspect is such that an insertion hole is formed in the blades; a fitting hole is formed in the side walls; fitting protrusions are formed on the two sides of the spacing maintenance member; and the fitting protrusions are inserted into the insertion holes in the blades and fitted into the fitting holes in the side walls so as to mount the spacing maintenance member and the blades between the side walls. Accordingly, blade mounting and medical knife assembly can be performed by inserting the fitting protrusions on the spacing maintenance member into the insertion holes in the blades, and fitting these fitting protrusions into the fitting holes in the side walls, which facilitates assembly and reduces manufacturing time.

The invention described in claim 8 is such that the handle has a top wall and a bottom wall in a forward portion thereof, on which fingertips can be placed during use, the top wall being formed in a first handle-constituting part and the bottom wall being formed in a second handle-constituting part. Accordingly, the top wall and the bottom wall can be used for finger placement when the knife is used, allowing for stable work. Furthermore, the handle-constituting parts respectively comprise the side walls and the top wall or bottom wall, the cross-sections of those portions each forming an L shape. Consequently, there will be no interference by the top wall or the bottom wall when the spacing between the two side walls is changed in the handle before being assembled.

DETAILED DESCRIPTION OF THE INVENTION

Figure 5:
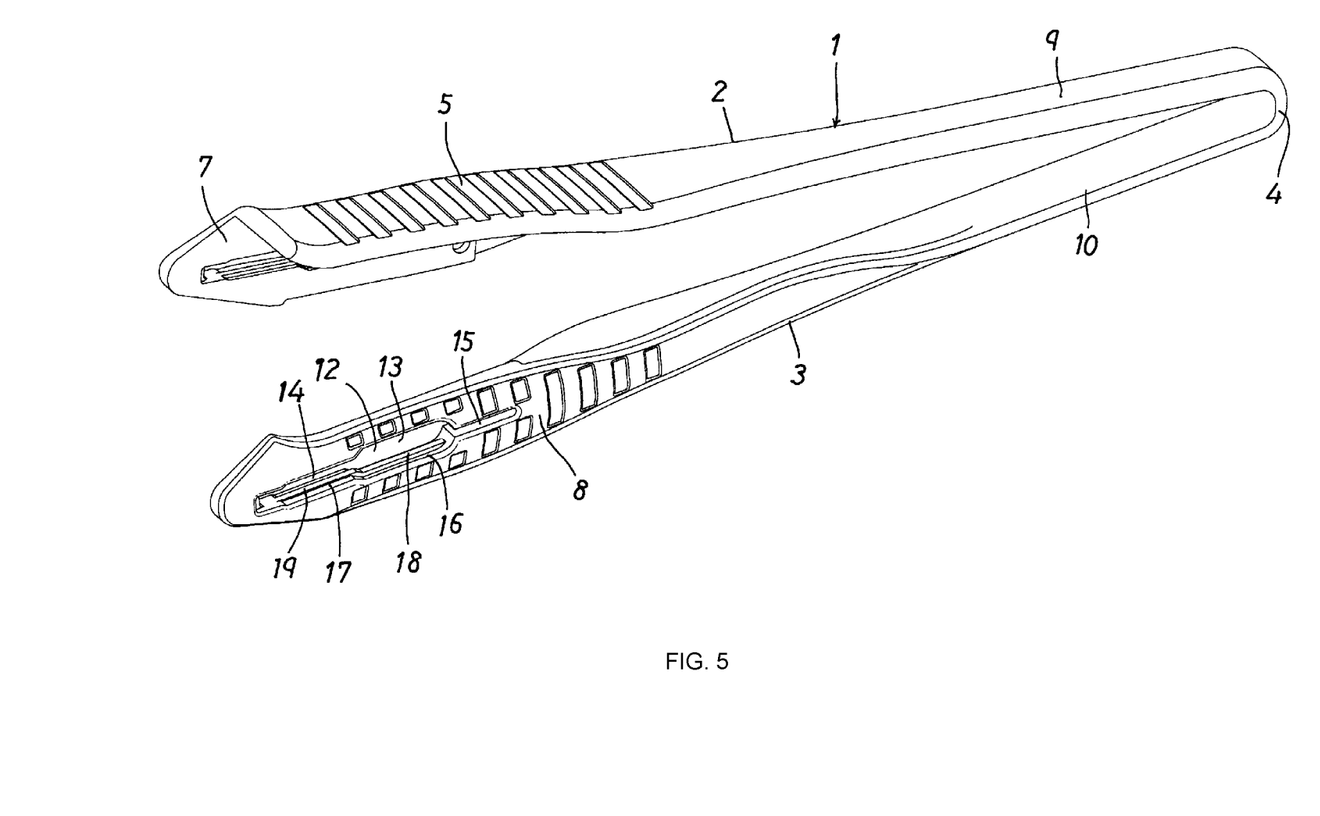
FIG. 5 is a perspective view of the handle before being assembled as a medical knife.
Figure 6:
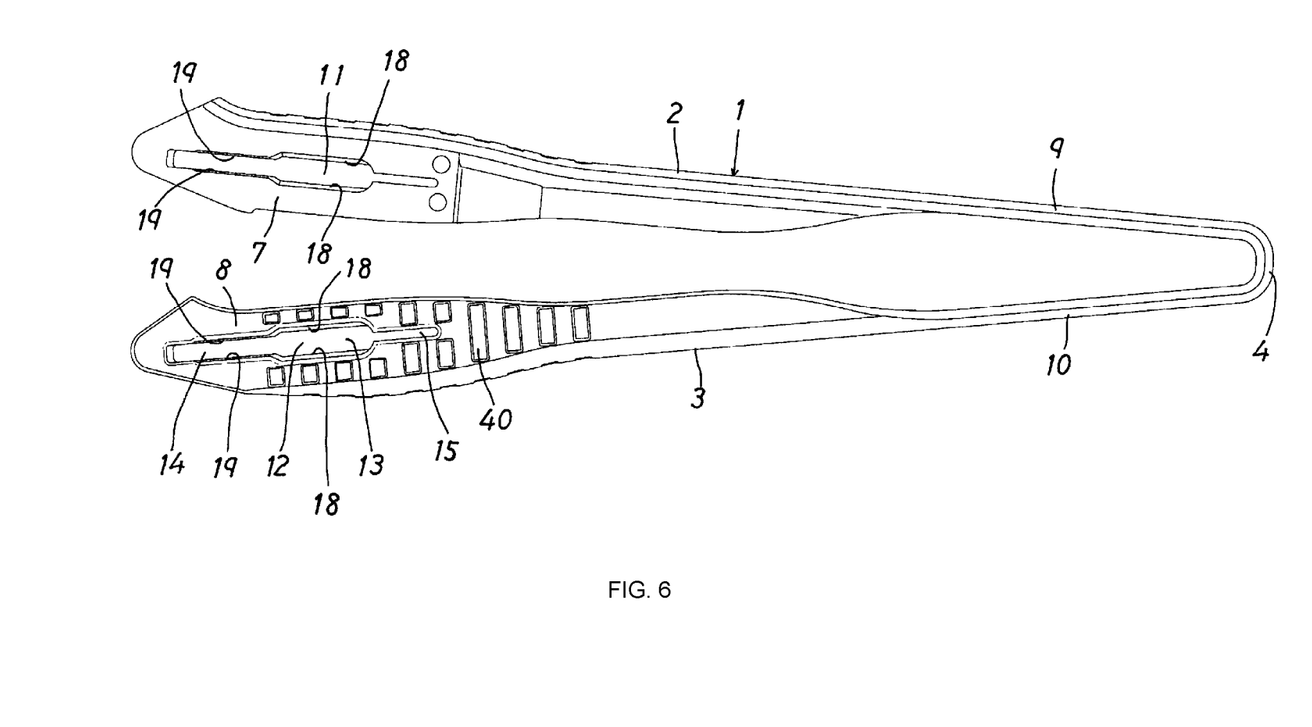
FIG. 6 is a side view of the handle before being assembled as a medical knife.
Figure 7:
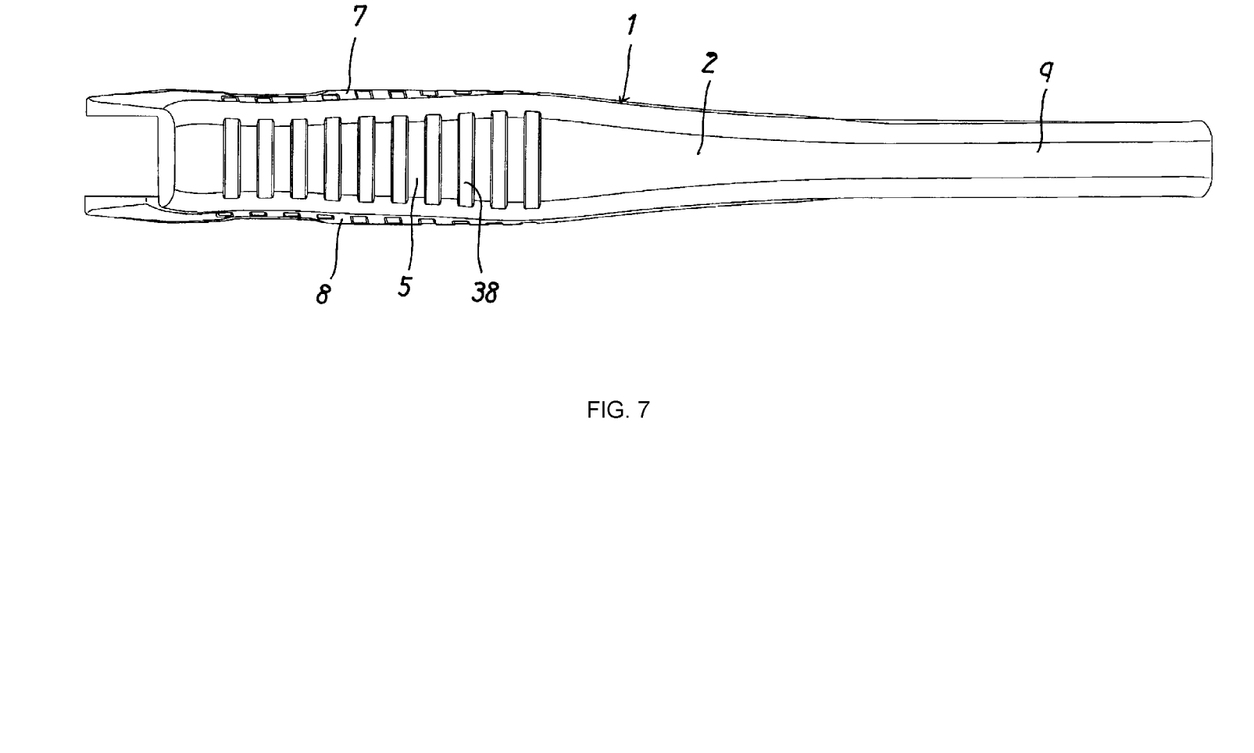
FIG. 7 is a top view of the handle before being assembled as a medical knife.

Next, embodiments of the present invention are described with reference to the drawings. Note that, in the present embodiment, the entire knife is disposable. As shown in FIG. 5 and FIG. 6, a handle 1 before being assembled in a medical knife is formed in the shape of tongs, and the handle-constituting parts 2, 3 of the handle 1 before assembly are formed in an already open configuration. Furthermore, as shown in FIG. 5, in the handle 1 before assembly, the handle-constituting parts 2, 3 face each other and, as shown in FIG. 7, these are formed in a configuration such that these are not offset from each other in the lateral width direction.

Figure 1:
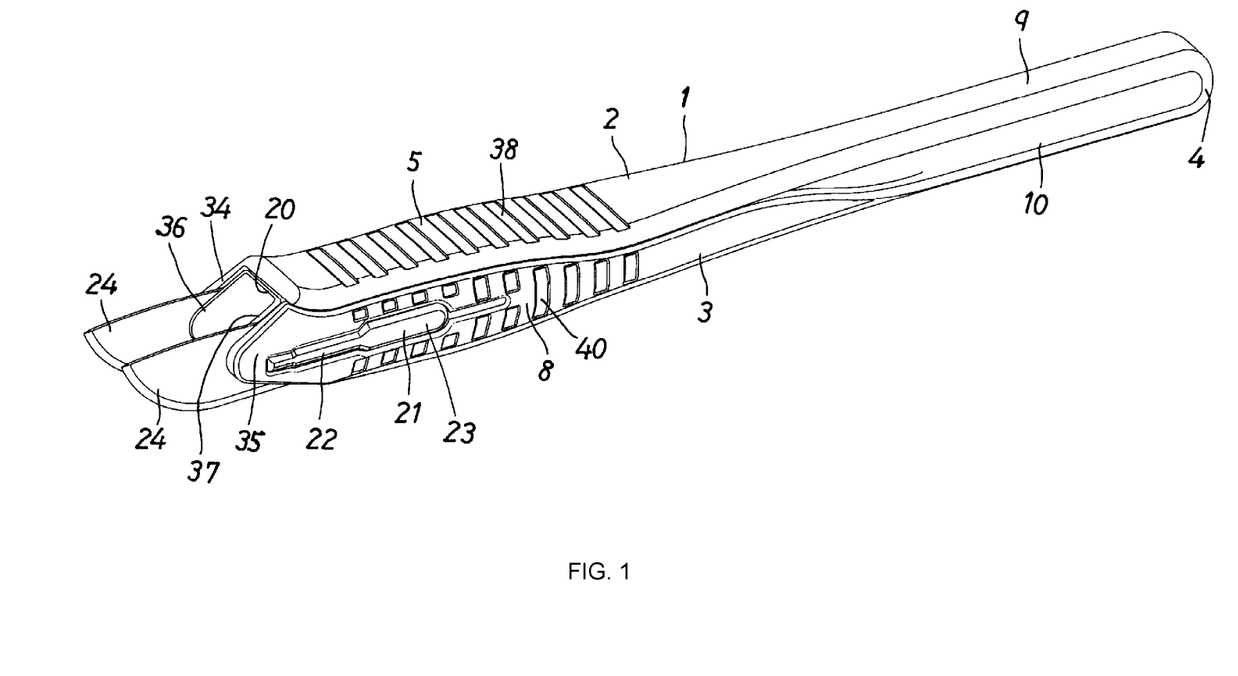
FIG. 1 is a perspective view of the present invention, seen from above.
Figure 2:
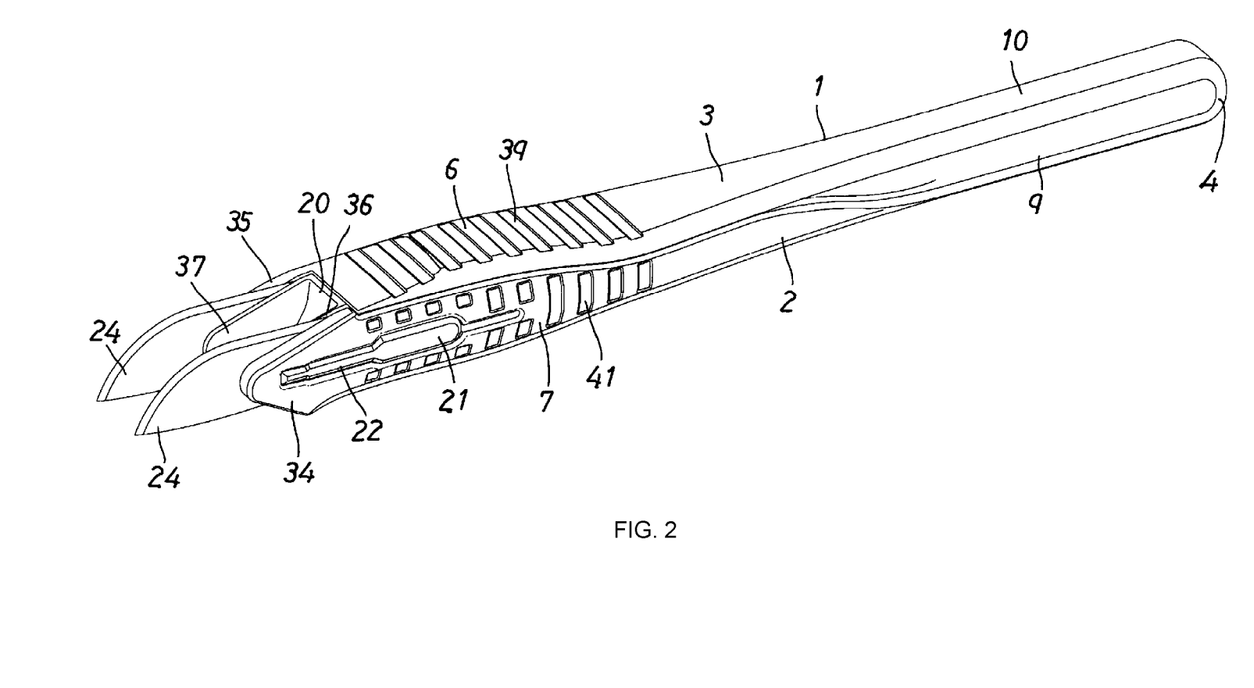
FIG. 2 is a perspective view of the present invention, seen from below.
Figure 3:
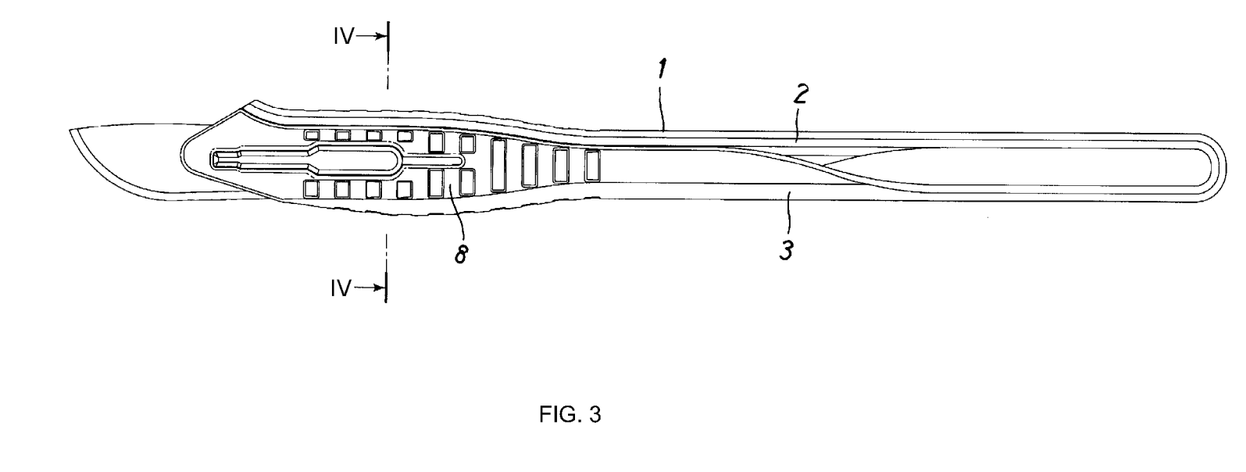
FIG. 3 is a side view of the present invention.

The handle 1 is formed from a flexible material, and for example, is integrally formed by injection molding a flexible thermoplastic resin such as polypropylene or polyethylene. The handle-constituting parts 2, 3 of the handle 1 are integrally joined by way of a U-shaped connecting part 4 at the rear ends thereof. As shown in FIG. 1 and FIG. 2, a top wall 5 and a bottom wall 6 are formed at the front of the handle 1, for placing fingertips during use. The top wall 5 and the bottom wall 6 are formed by way of the expansion of the lateral widths of the forward portions of the handle-constituting parts 2, 3, which extend forward from the connecting part 4 at the rear ends thereof, and a multiplicity of anti-slip grooves 38, 39 are formed on the surfaces thereof.

Further, side walls 7, 8 are formed at the front of the handle 1, and anti-slip grooves 40, 41 are formed at the surfaces. One of the side walls 7, is formed integrally with the top wall 5, so as to form a right angle therewith, and the other side wall 8 is formed integrally with the bottom wall 6, so as to form a right angle therewith. Accordingly, the handle-constituting parts 2, 3 respectively comprise the side walls 7, 8 and the top wall 5 or bottom wall 6, the cross-sections of those portions each forming an L shape. The portions having sections wherein the side walls 7, 8 and the top wall 5 or bottom wall 6 form an L shape will not bend under normal handling, even though the handle-constituting parts 2, 3 are formed from a flexible material. Conversely, the rearward portions 9, 10 of the handle-constituting parts 2, 3 have a planar section, and can therefore bend. Accordingly, starting from the situation shown in FIG. 6, it is possible to spread apart or close together the two handle-constituting parts 2, 3, centered on the connecting part 4, by bending the rearward portions 9, 10 of the handle-constituting part 2, 3. Consequently, the spacing between the top wall 5 and the bottom wall 6 can be made adjustable.

As described above, in the handle 1 before assembly, the handle-constituting parts 2, 3 face each other, without being offset with respect to each other in the lateral width direction, but because the rearward portions 9, 10 of the handle-constituting parts 2, 3 do not have an L shaped section, but rather are formed in a thin planar shape, they can be bent in the lateral width direction. Accordingly, the upper handle-constituting part 2 can be bent so as to rotate around the connecting part 4 in the clockwise direction with respect to the lower handle-constituting part 3, in the handle 1 as seen from above illustrated in FIG. 7. In this case, twisting of the connecting part 4 is added to the bending of the rearward portions 9, 10. Consequently, as seen from above, the two side walls 7, 8 can be distanced from each other such that the spacing therebetween is expanded.

As shown in FIG. 6, elongate fitting holes 11, 12 are respectively formed in both of the side walls 7, 8. Next, the configuration of the fitting holes 11, 12 will be described, but as the configurations are identical, only the fitting hole 12 will be described. The fitting hole 12 is formed in the shape of a slit, but rather than slit width of the fitting hole 12 being the same over the entire length thereof, the slit width is greatest in a fitting hole central part 13 of the fitting hole 12 and the slit width in a fitting hole front part 14 thereof is smaller than this, while the slit width in a fitting hole back part 15 thereof is even smaller. As described hereafter, the fitting hole back part 15 does not serve for fitting, but rather merely serves to elastically expand the slit width of the entire fitting hole 12.

As shown in FIG. 5, fitting ridges 18, 19 are provided continuously from the bottom face 16 of the fitting hole central part 13 to the bottom face 17 of the fitting hole front part 14. As shown in FIG. 6, fitting ridges similar to these fitting ridges 18, 19 are also formed on the upper faces of the fitting hole 12.

Figure 4:
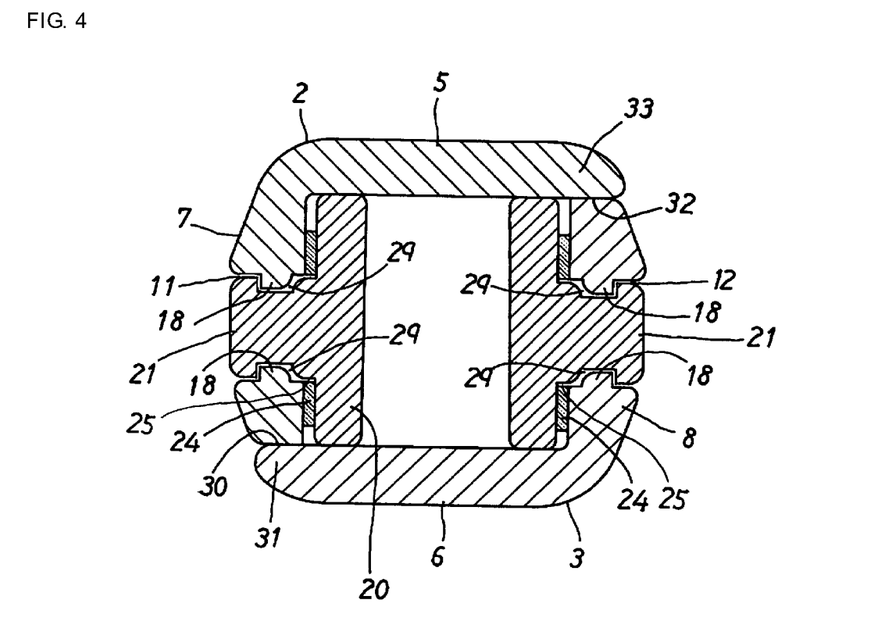
FIG. 4 is a sectional end of view at IV-IV in FIG. 3.
Figure 8:
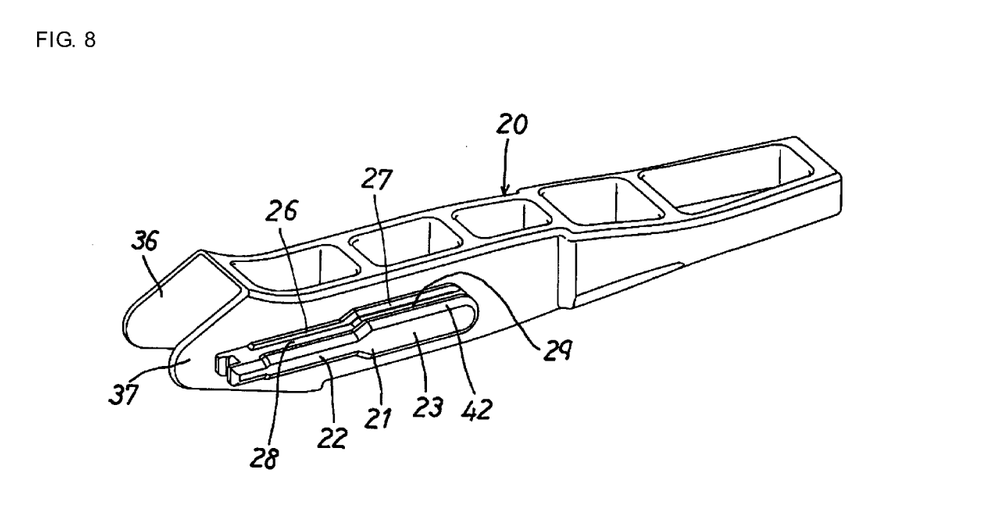
FIG. 8 is a perspective view of the space maintenance member.

In the present embodiment, a spacing maintenance member 20 is mounted between the two side walls 7, 8, in order to maintain the spacing between the two side walls 7 and 8 constant. As shown in FIG. 8, a fitting protrusion 21 (the other one is shown in FIGS. 2 and 4) is provided on both sides of the spacing maintenance member 20. The fitting protrusion 21 comprises a forward part 22 having a small vertical width, and a rearward portion 23, having a greater vertical width. The fitting protrusion 21 is formed in a shape such that it can be inserted into an insertion hole 25 in the blade 24, and is matched to the shape of this insertion hole 25.

Figure 9:
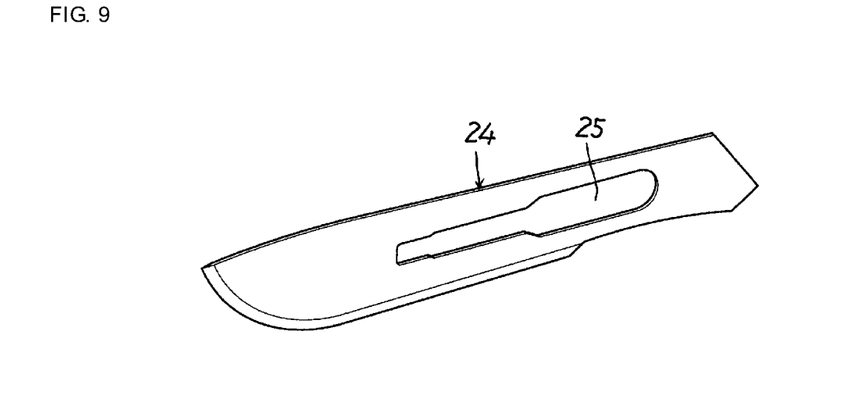
FIG. 9 is a perspective view of a blade.

Furthermore, the slit width of the fitting hole central part 13 is formed larger than the slit width of the fitting hole front part 14 in the fitting hole 12, as described above, in order to fit the fitting protrusion 21 into the fitting hole central part 13 and the fitting hole front part 14. Furthermore, fitting grooves 28, 29 are provided continuously from the top face 26 of the forward portion 22 to top face 27 of the rearward portion 23, on the fitting protrusion 21. Further, while not illustrated, a fitting groove is likewise provided continuously on the bottom face of the fitting protrusion 21. Note that the reason for which the shapes of the blade 24 and the insertion hole 25 therein are in the shapes illustrated in FIG. 9 is so that it is possible to use a blade commonly used as a conventional surgical scalpel blade directly, rather than the blade 24 being made for the present embodiment. Accordingly, in the present embodiment, a conventionally commonly used surgical scalpel blade can be used directly. It is, however a matter of course that use may be made of a blade specially made for the present invention in which the shape of the insertion hole 25 in this blade 24 and the shape of the fitting protrusions 21, 21 on the spacing maintenance member 20, which are inserted therein, differ from that of a commonly used surgical scalpel blade.

FIG. 4 is a sectional view showing the situation in which the handle-constituting parts 2, 3 of the handle 1, the spacing maintenance member 20, and a pair of blades 24, 24 are assembled in the present embodiment. The spacing maintenance member 20 is mounted between the two side walls 7, 8 of the handle-constituting parts 2, 3, and blades 24, 24 are respectively fitted between the two side walls 7, 8 and the spacing maintenance member 20. The fitting protrusions 21, 21 on the spacing maintenance member 20 are inserted into the insertion holes 25 in the respective blades 24, and fitted into the fitting holes 11, 12 in the two side walls 7, 8. The fitting ridges 18, 18 on the side walls 7, 8 fit into the respective fitting grooves 29 on the fitting protrusions 21, 21, resulting in a secure fit. Furthermore, while not illustrated in FIG. 4, fitting ridges 19, 19 on the side walls 7, 8 also fit into the respective fitting grooves 28 on the fitting protrusions 21, 21. The spacing between the two blades 24, 24 in FIG. 4 is 9 mm. When a medical knife with a spacing of 10 mm is to be produced, rather than needing to change the shape and size of the handle 1, it suffices to make a spacing maintenance member 20 having a width that is 1 mm wider, at 10 mm, and to mount this. When a spacing maintenance member 20 having a width of 10 mm is mounted between the two side walls 7, 8, the blades 24, 24 are fitted with the spacing between the side walls 7, 8 opened 1 mm further, by bending the handle-constituting parts 2, 3. At this point, the bottom edge 30 of the side wall 7 and the end 31 of the bottom wall 6 are slightly offset, and the top edge 32 of the side wall 8 and the end 33 of the top wall 5 are slightly offset, but these offsets are slight, and do not present a problem in terms of use. Furthermore, the side wall 7 and the top wall 5, as well as the side wall 8 and the bottom wall 6, respectively form sectional L shapes. Thus, the offset of the bottom edge 30 of the side wall 7 and the end 31 of the bottom wall 6, as well as the offset of the top edge 32 of the side wall 8 and the end 33 of the top wall 5, described above, occur at the underside of the top wall 5 and the topside of the bottom wall 6, and therefore there is no change in the surfaces of the top wall 5 and the bottom wall 6, on which the fingertips are placed, such that there will be no problems in placing the fingertips. Further, as shown in FIG. 1 and FIG. 2, the shape of the front end parts 34, 35 of the side walls 7, 8 and the front end parts 36, 37 of the spacing maintenance member 20 are formed substantially identical. Accordingly, the two blades 24, 24 are trapped from the two sides by the side walls 7, 8 and the spacing maintenance member 20, as far as the front end parts of the handle 1, such that the blades 20, 20 will not readily bend.

Next, a method of assembling the medical knife of this embodiment will be described. First, the spacing maintenance member 20 is fixed in place so that one of the fitting protrusions 21 is on top. Next, in order to set the blades 24 on the upper face of the spacing maintenance member 20, the fitting protrusion 21 on the top side of the spacing maintenance member 20 and the insertion hole 25 in the blade 24 are aligned and the blade 24 is placed on the upper face of the spacing maintenance member 20 so that the fitting protrusion 21 is inserted into the insertion hole 25 in the blade 24. Next, the handle 1, which was made by injection molding, is prepared with a first handle-constituting part 2 downward and a second handle-constituting part 3 upward. That is to say, the handle 1 shown in FIG. 6 is a top view of the prepared handle 1. In this state, the upper side wall 8 is overlaid on the spacing maintenance member 20 on which the blade 24 has been placed and the fitting protrusion 21 on the spacing maintenance member 20 is pushed into and fitted in the fitting hole 12 in the side wall 8. At this time, as shown in FIG. 8, the upper peripheral edge 42 of the fitting protrusion 21 is formed as an inclined face, and this inclined upper peripheral edge 42 is pushed in so as to push open the fitting hole 12. Then, the fitting hole 12 opens relatively easily due to the action of the fitting hole back part 15, and the fitting protrusion 21 fits into the fitting hole 12. Consequently, the blade 24 is fastened between the spacing maintenance member 20 and the side wall 8. Next, when the handle 1 is inverted with the spacing maintenance member 20 fitted in the side wall 8, the face of the spacing maintenance member 20 that was originally on the bottom becomes the upper face, and another blade 24 is set by being placed in that face that has become the upper face. Then, while closing together the handle-constituting parts 2, 3, centered on the connecting part 4, the side wall 7 of the first handle-constituting part 2 is overlaid on the spacing maintenance member 20 in which the blade 24 has been placed and the fitting protrusion 21 on the spacing maintenance member 20 is pushed and fitted into the fitting hole 11 in the side wall 7. In the same manner as when fitting the fitting protrusion 21 in the fitting hole 12 described above, at this time as well, the fitting hole 11 opens easily, allowing for fitting. By fitting the first fitting protrusion 21 and the fitting hole 12 and the second fitting protrusion 21 and the fitting hole 11, the fitting ridges 18, 18 on the side walls 7, 8 fit into the respective fitting grooves 29 on the fitting protrusions 21, 21 and the fitting ridges 19, 19 on the side walls 7, 8 fit into the respective fitting grooves 28 on the fitting protrusions 21, 21, resulting in a secure fit. Furthermore, in place of an assembly method of this sort, a method is also possible in which a blade unit is made in which a pair of blades 24, 24 are mounted in advance on both sides of the spacing maintenance member 20 using means such as adhesion, welding or caulking, and this blade unit is mounted between the two side walls 7, 8.

Next, the sizes in the present embodiment will be described. The overall length of the medical knife is approximately 148 mm, and the overall length of the handle 1, excluding the blade 20, is approximately 134 mm. The maximum lateral width of the handle 1 is approximately 16.5 mm, and the maximum thickness, which is to say the maximum vertical width is approximately 13.5 mm. The sizes are as described above, but it is a matter of course that the present invention is not limited to these numerical values.

Note that the present invention can be embodied in various different modes based on the configuration described above. For example, the connecting part 4 may be formed by a thin hinge, which is thinner than the thickness of the handle-constituting parts 2, 3. In this case, even if the handle-constituting parts 2, 3 are so thick as not to bend, by deforming the thin hinge, the handle 1 before being assembled in the medical knife will be such that the handle-constituting parts 2, 3 that are forward of the connecting part 4 can be spread apart or closed together, centered on the connecting part 4, such that the distance of the spacing between the two side walls 7, 8 can be made adjustable. Furthermore, as shown in FIG. 6, in the present embodiment, the handle 1 before being assembled in the medical knife is formed so that the two handle-constituting parts 2, 3 are already open, but this may also be formed so as to be closed from an open configuration, so that the side walls 7, 8 of the two handle-constituting parts 2, 3 form a pair with each other. In this case, in the manufacturing process, the two handle-constituting parts 2, 3 are set in the open configuration and the blades and the spacing maintenance member are overlaid on the lower side wall, from above. Furthermore, in the present invention, other blades may be added, in addition to the pair of blades, which are constituent elements. For example, another blade may be mounted in the center of the spacing maintenance member 20 by way of insert molding. Alternatively, a plurality of spacing maintenance members may be prepared, and blades may be trapped between these spacing maintenance members so as to make a unit.

With the configuration in which the two handle-constituting parts forward of the connecting part can be spread apart or closed together, centered on the connecting part, and the spacing distance between the two side walls is adjustable, it is possible to assemble medical knives having a pair of blades wherein the blade spacing is different, even though the handles are molded in the same shape.

The invention claimed is:

1. A disposable medical knife comprising a handle, a spacing maintenance member, and two blades, the handle comprising a pair of facing handle-constituting parts, each of the handle-constituting parts having, spaced from a proximal end of the handle, a side wall facing the side wall of the other handle-constituting part and the handle-constituting parts being joined by a connecting part forming the proximal end of the handle, the handle-constituting parts and the connecting part being integrally formed of the same flexible material which allows the two handle-constituting parts to be spread apart and closed together for assembling the disposable medical knife;

wherein:
a respective fitting hole is formed in each of the side walls;
a respective fitting protrusion is provided on each of respective sides of the spacing maintenance member facing respective said side walls;
each of the blades has an insertion hole; and
the spacing maintenance member is situated between the two side walls, and each of the blades is situated between a respective one of the sides of the spacing maintenance member and a respective one of the side walls, and each of the fitting protrusions on the spacing maintenance member is inserted through the insertion hole in a respective one of the blades and fitted into the fitting hole in a respective one of the side walls, whereby the blades are fixed between the spacing maintenance member and the side walls.

* * * * *